(12) United States Patent
Brandl et al.

(10) Patent No.: US 7,419,645 B2
(45) Date of Patent: Sep. 2, 2008

(54) DISINFECTING AND CLEANING AGENT CONNECTION DEVICE

(75) Inventors: Matthias Brandl, Bad Koenigshofen (DE); Elmar Wolter, Bad Koenigshofen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 570 days.

(21) Appl. No.: 10/930,955

(22) Filed: Sep. 1, 2004

(65) Prior Publication Data

US 2005/0047959 A1 Mar. 3, 2005

(30) Foreign Application Priority Data

Sep. 3, 2003 (DE) ................. 103 40 648

(51) Int. Cl.
*A61L 2/00* (2006.01)
(52) U.S. Cl. .................................... 422/292
(58) Field of Classification Search .......... 422/292
See application file for complete search history.

(56) References Cited

U.S. PATENT DOCUMENTS

| | | | | |
|---|---|---|---|---|
| 4,176,057 A * | 11/1979 | Wheatley et al. | ............. | 210/637 |
| 4,366,051 A * | 12/1982 | Fischel | ............. | 210/96.2 |
| 5,603,902 A * | 2/1997 | Maltais et al. | ............. | 422/103 |
| 5,624,551 A * | 4/1997 | Baumann et al. | ............. | 210/134 |
| 5,641,456 A * | 6/1997 | Rosenauer | ............. | 422/29 |
| 5,651,893 A * | 7/1997 | Kenley et al. | ............. | 210/636 |
| 5,656,027 A * | 8/1997 | Ellingboe | ............. | 604/541 |
| 5,895,578 A * | 4/1999 | Simard et al. | ............. | 210/636 |
| 6,022,512 A * | 2/2000 | Tanaka et al. | ............. | 422/292 |
| 6,051,188 A * | 4/2000 | Spickermann | ............. | 422/30 |
| 6,251,279 B1 * | 6/2001 | Peterson et al. | ............. | 210/636 |
| 6,299,076 B1 * | 10/2001 | Sloan et al. | ............. | 239/136 |
| 6,468,472 B1 * | 10/2002 | Yu et al. | ............. | 422/28 |
| 2002/0179518 A1 * | 12/2002 | Ho | ............. | 210/321.71 |

FOREIGN PATENT DOCUMENTS

| | | |
|---|---|---|
| DE | 43 21 008 C1 | 5/1994 |
| EP | 1 437 547 A2 | 7/2004 |
| EP | 1437547 A2 * | 7/2004 |
| GB | 1 216 628 | 12/1970 |

* cited by examiner

*Primary Examiner*—Walter D. Griffin
*Assistant Examiner*—Lydia Edwards
(74) *Attorney, Agent, or Firm*—Jacobson Holman PLLC

(57) ABSTRACT

A disinfecting and cleaning agent connection device for devices with a chamber for the holding or transport of fluids has a connection line that connects the fluid chamber with a disinfecting or cleaning agent container. The connection device has a connection line, a buffer chamber, a sealing element in the upper section of the buffer chamber connecting it with the fluid chamber, a channel which opens into the bottom section of the buffer chamber and has a siphon-type section whose end lies lower than the bottom of the buffer chamber, and a fluid sensor in the buffer chamber which is lower than the upper section of the siphon area and higher than the channel opening into the buffer chamber. The disinfecting and cleaning agent connection device can be used in conjunction with medical devices such as a dialysis machine and a reverse osmosis machine.

14 Claims, 1 Drawing Sheet

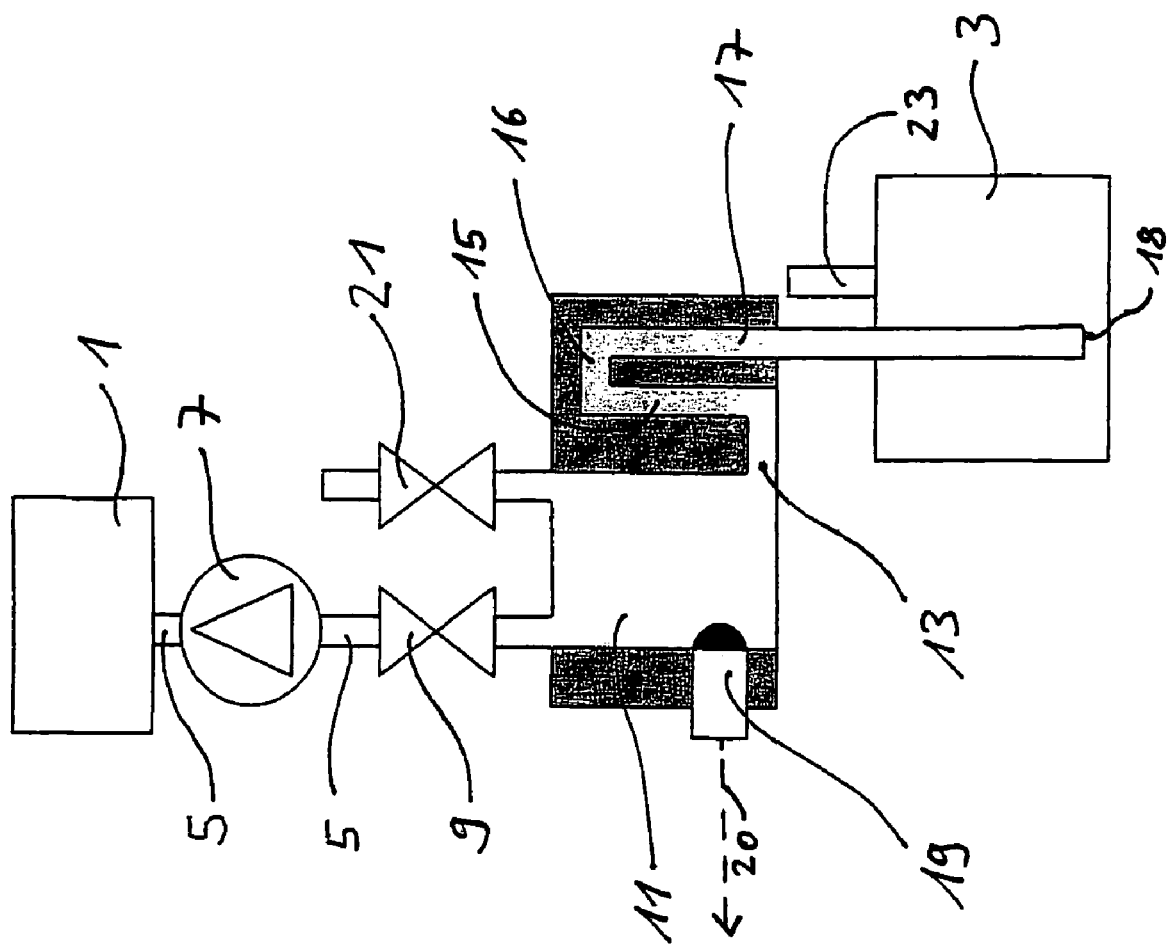

DISINFECTING AND CLEANING AGENT CONNECTION DEVICE

BACKGROUND OF THE INVENTION

1. Field of Invention

The invention refers to a disinfecting and cleaning agent connection device for devices which have a chamber for the holding or transport of fluids with a connection line for connection of the fluid chamber with a disinfecting or cleaning agent container.

To clean medical devices which have a liquid circulation system for medical fluids, disinfecting agents or special cleaning agents are passed through the fluid circulation system. When a disinfecting agent container is connected to such a medical device, e.g. a dialysis system, disinfecting agent must be prevented from unintentionally penetrating the system.

On the other hand, during the normal operation of the medical device, no fluid should flow from the medical device into the disinfecting agent container, thereby diluting the disinfecting agent in an uncontrolled manner.

2. Description of the Prior Art

In the known solutions, a corresponding arrangement of check valves and controlled solenoid valves are used. In DE 43 21 008 C1 a buffer volume is provided in which the pressure differs from that in the rest of the supply line so that the density can be monitored. The pressure of the buffer volume is monitored. If the pressure in the buffer volume changes, this indicates a leak in one of the valves connected to the buffer volume.

SUMMARY OF THE INVENTION

The object of the current invention is to provide a disinfecting and cleaning agent connection device which, on the one hand, is simple and economical and, on the other hand, ensures a high degree of reliability, particularly for medical applications. This object is attained using a disinfecting and cleaning agent connection device that includes a buffer chamber, a sealing element in an upper section of the buffer chamber, a channel which opens into a bottom portion of the buffer chamber and which has a siphon-type section, and a fluid sensor in the buffer chamber which is located at a level lower than an upper section of the siphon section and higher than the channel opening. Other advantageous embodiments of the present invention are described herein. The object is also met with a medical device that includes the connection device, a reverse osmosis system that includes the connection device, or a dialysis system that includes the connection device. Advantageous applications of the aforementioned embodiments are also described herein.

The following describes the use of the invention with medical devices or medical fluids in which reliable operation is a particular advantage. The invention can however, be used equally for non-medical devices.

The disinfecting and cleaning agent connection device in accordance with the invention has a connection line on the fluid chamber which is provided to hold or transport medical fluids with a disinfecting agent container with an area which forms a buffer chamber. In the upper section of the buffer chamber there is a sealing element connecting the buffer chamber to the fluid chamber. The disinfecting and cleaning agent connection device in accordance with the invention also has a channel which opens into the lower part of the buffer chamber. The channel has a siphon-type section which, proceeding from the opening, has a section pointing upwards, an upper section and a section pointing downwards, whereby the end of the section pointing downwards lies lower than the floor of the chamber. The disinfecting and cleaning agent connection device in accordance with the invention also has a fluid sensor in the buffer chamber which is arranged at a level lower than the upper part of the siphon section of the channel and higher than the channel opening into the buffer chamber.

When we refer in the following to disinfecting agent, this also generally includes other cleaning agents.

The buffer chamber can, for example, be a rigid container, a pipe segment or a tube segment. The sealing element can, for example, be a valve or a flow-interrupting pump. For the sake of simplification, the following assumes a valve as a sealing element.

During normal operation the buffer chamber is connected to the fluid chamber of the medical device with the aid of the valve. The lower end of the channel is immersed in a disinfecting or cleaning agent canister. During normal operation of the medical device the valve is closed so that no medical fluid can leak from the medical device into the disinfecting agent container and no disinfecting agent can leak into the medical device. In the event of a fault in the valve, medical fluid leaks through the valve into the buffer chamber. This gradually fills up with the leaking fluid until the fluid sensor detects the leaking fluid and, for example, gives an alarm signal and interrupts the treatment as necessary.

Due to the siphon-type connection of the buffer chamber to the disinfecting agent container, any medical fluid which enters the buffer chamber is effectively prevented from flowing directly into the disinfecting agent container, thereby diluting or altering the disinfecting agent in an uncontrolled manner.

If, due to a fault during normal operation, the valve between the fluid chamber and the disinfecting agent container should be open and the pump provided to convey the disinfecting agent into the medical device is in operation, disinfecting agent flows from the disinfecting agent container through the siphon-type channel in an uncontrolled manner into the buffer chamber. The fluid sensor registers this and the fault is detected.

During cleaning, cleaning agent is pumped into the medical device through the channel, the buffer chamber and the now open valve. When cleaning is completed, the disinfecting agent is drained off. It runs through the open valve into the buffer chamber and fills this to a level corresponding to the upper section of the siphon-type drainage channel. Now the fluid is drained by the siphon into the disinfecting agent canister via the now communicating tubes. The fact that the siphon-type channel opens into the buffer chamber at the very bottom ensures that the whole buffer chamber is evacuated in accordance with the principle of communicating tubes.

The disinfecting and cleaning agent connection device for medical devices in accordance with the invention therefore guarantees maximum safety and simple handling. In normal operation of the medical device any leaks in the locking valve between the fluid chamber and the disinfecting agent container are reliably detected. After cleaning the medical device with disinfecting agent, the specially shaped siphon-type drain ensures that all of the disinfecting agent is drained out of the buffer chamber and the connection to the disinfecting agent container into the disinfecting agent container. The device in accordance with the invention thus ensures that the medical fluid cannot be contaminated by the disinfecting agent and the disinfecting agent in the canister cannot be altered or diluted in an uncontrolled manner by the medical fluid. This means that the disinfecting agent container can remain connected to the medical device at all times.

Any uncontrolled leak of disinfecting agent into the medical device in the case of a faulty pump or valve is detected by the uncontrolled flow at the fluid sensor.

If, in accordance with a preferred embodiment, the buffer chamber has a larger cross section than the connected sections of the line, this ensures particularly reliable operation.

A disinfecting agent and cleaning agent connection device in accordance with the invention with an even higher degree of safety has, preferentially, an air valve in the upper section of the buffer chamber. During normal operation of the medical device, during which the locking valve between the disinfecting agent container and the fluid chamber should be closed for medical fluid, this air valve on the buffer chamber is open. If, due to a fault, the locking valve between the fluid chamber and the disinfecting agent container is open, and the pump provided to convey the disinfecting agent into the medical device is in operation, this open air valve prevents disinfecting agent from being pumped into the medical device. Instead, only air is drawn through the open air valve and the buffer chamber into the medical device. During cleaning, the air valve is closed so that the disinfecting agent can be drawn from the container into the medical device.

Various types of sensor can be used as a fluid sensor. A conductivity sensor, for example, can be used which monitors the conductivity of the surrounding medium and gives a signal when it become wet. In one particularly advantageous embodiment an optical fluid sensor is used which can monitor fluid at extremely low or even no conductivity. The function of the optical sensor can be easily and automatically checked by a periodic function test.

The disinfecting agent and cleaning agent connection device in accordance with the invention can be used particularly advantageously with medical devices in which medical fluids have to be transported in fluid circulations systems in a highly sensitive manner, e.g. dialysis machines or reverse osmosis systems.

BRIEF DESCRIPTION OF THE DRAWINGS

An embodiment of the disinfecting agent and cleaning agent connection device is explained in detail in the attached drawing.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

1 shows a medical device with a fluid circulation system, e.g. a dialysis machine. The dialysis machine is connected via a connection line 5 which has a pump 7. A locking valve 9 connects the dialysis machine 1 with a buffer chamber 11. Alternatively the locking valve 9 can be omitted and the pump 7 provided as a flow-interrupting pump. The buffer chamber 11 preferentially has a larger cross section than the line 5. In the direct vicinity of the bottom of the buffer chamber 11 a channel ends with the channel opening 13 into the buffer chamber 11 which is in the shape of a siphon with a section 15 pointing upwards, an upper section 16 and a section 17 pointing downwards. The section 17 pointing downwards is immersed in a disinfecting agent canister 3. The end 18 of the section 17 pointing downwards is arranged in the bottom section of the canister 3 and lies lower than the floor of the buffer chamber 11. An optical fluid sensor 19 is provided in the lower section of the buffer chamber, but above the channel opening 13. For simplification sake, the drawing does not show the energy supply lines to the fluid sensor 19. 20 is a diagram of a signal line with the aid of which the signal from the fluid sensor 19 can be passed onto an evaluation or warning device.

An air valve 21 is provided in the upper section of the buffer chamber 11. The disinfecting agent container 3 has a ventilation valve 23.

The embodiment in accordance with the invention is used as follows: During the normal operation of the dialysis machine 1, the pump 7 is switched off and the valve 9 closed. The air valve 21 is open. The dialysis machine works in the familiar manner to clean the blood of a patient. The disinfecting agent container 3 contains disinfecting agent which is not being used during the normal operation of the dialysis machine 1. The buffer chamber is empty.

If there is a fault or a leak in the valve 9, the medical fluid leaks from the dialysis machine 1 through the valve 9 into the buffer chamber 11. Due to the siphon-type design of the drainage channel 15, 16, 17, the buffer chamber 11 first fills up with the medical fluid. As soon as the fluid level has reached the fluid sensor 19, this gives a signal via signal line 20 to an alarm device not shown in the drawing, e.g. an acoustic or optical alarm. It can also be arranged in such a way that the signal is used to automatically interrupt the medical treatment. The siphon-type design of the connection 13, 15, 16, 17 of the buffer chamber 11 with the disinfecting agent container 3 ensures that the medical fluid leaking though the valve 9 into the buffer chamber 11 cannot penetrate into the disinfecting agent container 3. The disinfecting agent therein can thus not be contaminated by the medical fluid.

If, however, during normal use of the dialysis machine 1 in the embodiment described here, the air valve 21 is closed and, due to a fault or an operator error during dialysis, valve 9 is unintentionally opened and/or pump 7 is switched on, disinfecting agent will leak in an uncontrolled manner through the channel 15, 16, 17 into the buffer chamber 11. The fluid sensor 19 responds and the corresponding alarm signal is given via signal line 20. Due to the buffer chamber 11 and the opening of the channel 13 into the lower section of the buffer chamber, no disinfecting agent can penetrate into the dialysis device 1. In addition to this, during normal use of the dialysis machine 1, the air valve 21 is open so that the suction of the disinfecting agent into the dialysis machine 1 through a possibly faulty pump 7 is practically ruled out by the design. Instead, only air can pass through the air valve 21 and the buffer chamber 11 into the dialysis machine 1.

After dialysis treatment the dialysis machine 1 has to be cleaned. For this purpose the valve 9 is opened and the pump 7 switched on. The air valve 21 is closed. Disinfecting agent is pumped from the disinfecting agent container 3 through the channel 15, 16, 17 and through the buffer chamber 11 into the dialysis device 1 and used there for cleaning. When cleaning is completed the pump 7 is switched off and valve 9 closed. The buffer chamber 11 and the siphon-type drain 13, 15, 16, 17 are filled with disinfecting agent. When the air valve 21 is opened, the disinfecting agent flows out of the buffer chamber 11 and the siphon-type drain into the disinfecting agent container. As this and the end 18 of the siphon-type drain are below the buffer chamber, the channel 15, 16, 17 and the buffer chamber 11 are completely evacuated by the siphon drain 15, 16, 17 in accordance with the principle of communicating tubes.

The device in accordance with the invention is inexpensive and can be realised with simple electronics. The unintentional penetration of toxic fluid is ruled out. Any leaks from the disinfecting agent canister to the medical device or from the medical device to the disinfecting agent canister are reliably detected. The device in accordance with the invention allows the detection of even tiny leaks, e.g. smaller than 1 ml per day.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A medical device with a disinfecting and cleaning agent connection device, said connection device comprising:
    a connection line configured to connect a fluid chamber for holding or transporting fluids with a disinfecting and cleaning agent container;
    a buffer chamber with a cross section preferentially larger than a cross section of parts of the connection line connected to the buffer chamber;
    a sealing element in an upper section of the buffer chamber connecting it to the fluid chamber;
    a channel which opens into a bottom of the buffer chamber and has a siphon-type section which, proceeding from a channel opening into the buffer chamber, has a section pointing upwards, an upper section, and a section pointing downwards, the end of the section pointing downwards lying lower than the floor of the buffer chamber; and
    a fluid sensor in the buffer chamber which is arranged at a level lower than the upper section of the siphon section and higher than the channel opening of the channel in the buffer chamber.

2. The medical device in accordance with claim 1, further comprising an air valve in the upper section of the buffer chamber.

3. The medical device in accordance with claim 1, wherein the fluid sensor is an optical sensor.

4. The medical device according to claim 1, further comprising a ventilation valve in an upper section of the disinfecting and cleaning agent container.

5. The medical device according to claim 1, wherein the sealing element is a valve.

6. A dialysis machine with a disinfecting and cleaning agent connection device, said connection device comprising:
    a connection line configured to connect a fluid chamber for holding or transporting fluids with a disinfecting and cleaning agent container;
    a buffer chamber with a cross section preferentially larger than a cross section of parts of the connection line connected to the buffer chamber;
    a sealing element in an upper section of the buffer chamber connecting it to the fluid chamber;
    a channel which opens into a bottom of the buffer chamber and has a siphon-type section which, proceeding from a channel opening into the buffer chamber, has a section pointing upwards, an upper section, and a section pointing downwards, the end of the section pointing downwards lying lower than the floor of the buffer chamber; and
    a fluid sensor in the buffer chamber which is arranged at a level lower than the upper section of the siphon section and higher than the channel opening of the channel in the buffer chamber.

7. A reverse osmosis system with a disinfecting and cleaning agent connection device, said connection device comprising:
    a connection line configured to connect a fluid chamber for holding or transporting fluids with a disinfecting and cleaning agent container;
    a buffer chamber with a cross section preferentially larger than a cross section of parts of the connection line connected to the buffer chamber;
    a sealing element in an upper section of the buffer chamber connecting it to the fluid chamber;
    a channel which opens into a bottom of the buffer chamber and has a siphon-type section which, proceeding from a channel opening into the buffer chamber, has a section pointing upwards, an upper section, and a section pointing downwards, the end of the section pointing downwards lying lower than the floor of the buffer chamber; and
    a fluid sensor in the buffer chamber which is arranged at a level lower than the upper section of the siphon section and higher than the channel opening of the channel in the buffer chamber.

8. A medical device with a disinfecting and cleaning agent connection device, said connection device comprising:
    a fluid connection line configured to connect a medical fluid chamber with a disinfecting and cleaning agent container;
    a buffer chamber in communication with the connection line, the buffer chamber having a cross section that is larger than a cross section of parts of the connection line that are in communication with the buffer chamber;
    a sealing element located in an upper section of the buffer chamber that is in communication with the fluid chamber;
    a channel in communication with a bottom section of the buffer chamber, the channel having a section configured as a siphon that includes a first vertically oriented section, a second vertically oriented, section in communication with the disinfecting and cleaning agent container, an upper section in communication with the first and second vertically oriented sections, and a lower section in communication with the buffer chamber and the first vertically oriented section, an end of the second vertically oriented section being lower than a floor of the buffer chamber; and
    a sensor configured to detect a fluid level in the buffer chamber, the sensor being located at a level lower than the upper section of the siphon section and higher than an opening of the lower channel section into the buffer chamber.

9. The medical device according to claim 8, wherein the sensor detects the level of the medical fluid or the level of the disinfecting and cleaning agent.

10. The medical device according to claim 8, wherein the channel siphon section is configured to prevent the medical fluid from entering the disinfecting and cleaning agent container, and to prevent the disinfecting and cleaning agent from entering the medical fluid chamber.

11. The medical device according to claim 8, wherein the sensor is a conductivity sensor.

12. The medical device according to claim 8, further comprising an air valve located in the upper section of the buffer chamber, the air valve being configured to open such that disinfecting and cleaning agent accumulated in the buffer chamber flows out of the buffer chamber and the channel siphon section and into the disinfecting and cleaning agent container.

13. A method of cleaning a medical device having a cleaning agent connection device that includes a connection line configured to connect a medical fluid chamber with a cleaning agent container, a buffer chamber with a cross section larger than a cross section of parts of the connection line connected to the buffer chamber and having an air valve in an upper section, a sealing element in an upper section of the buffer chamber that connects to the medical fluid chamber, a pump disposed between the sealing element and the medical fluid chamber, a channel which opens into the bottom of the buffer chamber and has a siphon section which, proceeding from a channel opening into the buffer chamber, has a section pointing upwards, an upper section, and a section pointing downwards, the end of the section pointing downwards lying lower than the floor of the buffer chamber, and a fluid sensor in the buffer chamber which is arranged at a level lower than the upper section of the siphon section and higher than the channel opening of the channel in the buffer chamber, the method comprising the steps of:

pumping the cleaning agent from the cleaning agent container into the medical fluid chamber; and draining unused cleaning agent from the buffer chamber and the siphon section into the cleaning agent container.

14. The method according to claim 13, further comprising the steps of before the step of pumping the cleaning agent, opening the sealing element and closing the air valve;

after the step of pumping the cleaning agent, discontinuing the pumping and closing the sealing element; and opening the air valve to drain the unused cleaning agent from the buffer chamber and the siphon section into the cleaning agent container.

\* \* \* \* \*